(12) United States Patent
Jablonski

(10) Patent No.: US 9,597,474 B2
(45) Date of Patent: Mar. 21, 2017

(54) PATIENT INTERFACE DEVICE WITH AUTO-ADJUSTING CUSHION

(75) Inventor: Gregory John Jablonski, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 613 days.

(21) Appl. No.: 13/818,181

(22) PCT Filed: Aug. 18, 2011

(86) PCT No.: PCT/IB2011/053645
§ 371 (c)(1),
(2), (4) Date: Feb. 21, 2013

(87) PCT Pub. No.: WO2012/028988
PCT Pub. Date: Mar. 8, 2012

(65) Prior Publication Data
US 2013/0152938 A1   Jun. 20, 2013

Related U.S. Application Data

(60) Provisional application No. 61/378,101, filed on Aug. 30, 2010.

(51) Int. Cl.
*A61M 16/06* (2006.01)
*A62B 18/02* (2006.01)
(Continued)

(52) U.S. Cl.
CPC .... *A61M 16/0683* (2013.01); *A61M 16/0057* (2013.01); *A61M 16/06* (2013.01);
(Continued)

(58) Field of Classification Search
CPC ...... A61M 16/06–16/0694; A62B 7/00; A62B 7/14; A62B 18/00; A62B 18/02;
(Continued)

(56) References Cited

U.S. PATENT DOCUMENTS 7,997,267 B2    8/2011  Ging
2004/0226566 A1* 11/2004  Gunaratnam et al. ... 128/207.18
(Continued)

FOREIGN PATENT DOCUMENTS

CN    102458547 A    5/2012
EP     2022528 A2   11/2009
(Continued)

OTHER PUBLICATIONS

Philips Respironics Masks for CPAP/BiPAP/BiLEVEL, Jun. 21, 2010 http://www.directhomemedical.com/index-respironics-products.html.
(Continued)

*Primary Examiner* — Tan-Uyen (Jackie) T Ho
*Assistant Examiner* — Ned T Heffner
(74) *Attorney, Agent, or Firm* — Michael W. Haas

(57) ABSTRACT

A patient interface device (2) includes a frame member (4) and a cushion (6) having a main body, a sealing portion, and first and second posts extending from the main body. The frame member defines a first orifice and a second orifice. The first post of the cushion is rotateably received within the first orifice and the second post is rotateably received within the second orifice in a manner that permits the cushion to rotate relative to the frame member.

11 Claims, 7 Drawing Sheets

(51) Int. Cl.
*A62B 18/08* (2006.01)
*A61M 16/00* (2006.01)
*A61M 16/08* (2006.01)

(52) U.S. Cl.
CPC .... *A61M 16/0666* (2013.01); *A61M 16/0816* (2013.01); *A61M 16/0875* (2013.01); *A61M 2210/0618* (2013.01)

(58) Field of Classification Search
CPC ................ A62B 18/04; A62B 18/06; A62B 18/08–18/088; B63C 11/12; B63C 11/18
See application file for complete search history.

(56) References Cited

U.S. PATENT DOCUMENTS

2007/0028919 A1\* 2/2007 Ho .......................... 128/204.18
2007/0044804 A1\* 3/2007 Matula et al. ........... 128/206.21
2009/0101141 A1 4/2009 Ging
2010/0012129 A1 1/2010 Kwok

FOREIGN PATENT DOCUMENTS

| JP | 2004000571 A | 1/2004 |
| JP | 2005537904 A | 12/2005 |
| JP | 2010119895 A | 6/2010 |
| WO | WO2004022145 A1 | 3/2004 |
| WO | WO2008106716 A1 | 9/2008 |
| WO | WO2009052560 A1 | 4/2009 |
| WO | WO2010135785 A1 | 12/2010 |

OTHER PUBLICATIONS

CPAP Mask, Jun. 21, 2010 http://search.cpapxchange.com/cpap-mask--list.

\* cited by examiner

PATIENT INTERFACE DEVICE WITH AUTO-ADJUSTING CUSHION

CROSS-REFERENCE TO RELATED APPLICATIONS

This patent application claims the priority benefit under 35 U.S.C. §371 of international patent application no. PCT/IB2011/053635, filed Aug. 18, 2011, which claims the priority benefit under 35 U.S.C. §119(e) of U.S. Provisional Application No. 61/378,101 filed on Aug. 30, 2010, the contents of which are herein incorporated by reference.

BACKGROUND OF THE INVENTION

1. Field of the Invention

The present invention relates to patient interface devices for communicating a flow of gas with an airway of a user, and, in particular, to a patient interface device having a structure that includes controlled flexing and auto-adjustment of a cushion relative to a frame.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Patients that that require pressure support therapy are often confronted with the problem of finding a suitable patient interface device. In finding a suitable patient interface device, such patients frequently struggle with issues relating to the seal and stability of the patient interface device, the comfort of the patient interface device, the size/weight of the patient interface device, and the sizing of the patient interface device. These challenges, if not addressed properly, can compromise the patient's compliance with the prescribed therapy.

More specifically, during the night, the stability of a mask seal will be challenged by the patient moving about in his or her bed. The changing head position can lead to air delivery hose torque and general interference with other objects (e.g. pillows, sheets, blankets, etc.). Thus, stability, and consequently seal, is a challenge for any patient interface device in the market.

In addition, patient comfort is an important factor, and can be negatively impacted in many ways. For example, over-tightening of the headgear (to compensate for lack of seal and stability) can increase pressure on the face and head, which in turn can result in pressure points and/or skin breakdown. Other components of the patient interface device (e.g. straps, frames, headgear, etc.) can also add discomfort for the patient because the geometry of such components can conflict with facial structures.

Furthermore, the general weight of the patient interface device can negatively impact a patient's experience by causing additional facial pressure or compounding over-tightening issues. Patient interface device weight can also negatively affect the seal and stability. Certain patients also have problems with a patient interface device interfering with his or her line of sight, and overall patient interface device size has been known to cause claustrophobia is some patients.

Finally, properly sizing a patient interface device can be difficult because facial structures vary greatly among patients. Not all patient interface devices are able to accommodate this range of differences, thus requiring either more sizes/variations or not providing an optimal fit for the majority of the user population.

SUMMARY OF THE INVENTION

Accordingly, it is an object of the present invention to provide a patient interface device that overcomes the shortcomings of conventional patient interface device. This object is achieved according to one embodiment of the present invention by providing a patient interface device that includes a frame member and a cushion having a main body, a sealing portion coupled to the main body, and a first post extending from a first side of the main body and second post extending from a second side of the main body. The frame member defines a first orifice and a second orifice. The first post of the cushion is rotateably received within the first orifice and the second post is rotateably received within the second orifice in a manner that permits the cushion to rotate relative to the frame member.

In another embodiment, a method of adjusting a patient interface device is provided that includes donning a patient interface device as just described, and causing the cushion to rotate relative to the frame member when the sealing portion is engaged with the face of the patient.

In still another embodiment, a cushion for a patient interface device includes a main body, a sealing portion coupled to the main body, a first post extending from a first side of the main body and structured to be rotateably received within a first orifice of a frame member of the patient interface device, and a second post extending from a second side of the main body and structured to be rotateably received within a second orifice of a frame member of the patient interface device.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
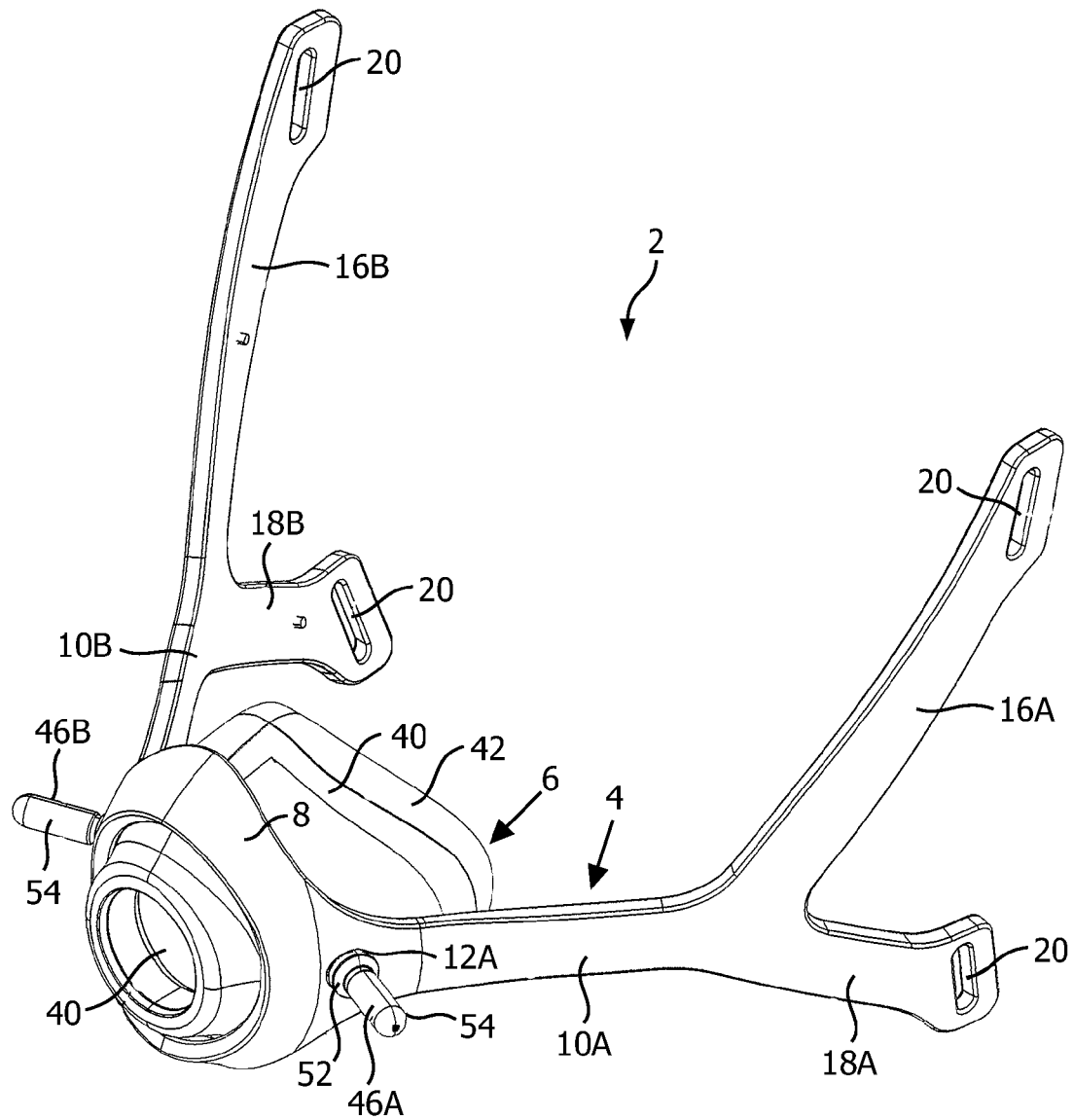
FIG. 1 is a front perspective view of a patient interface device according to an exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 9:
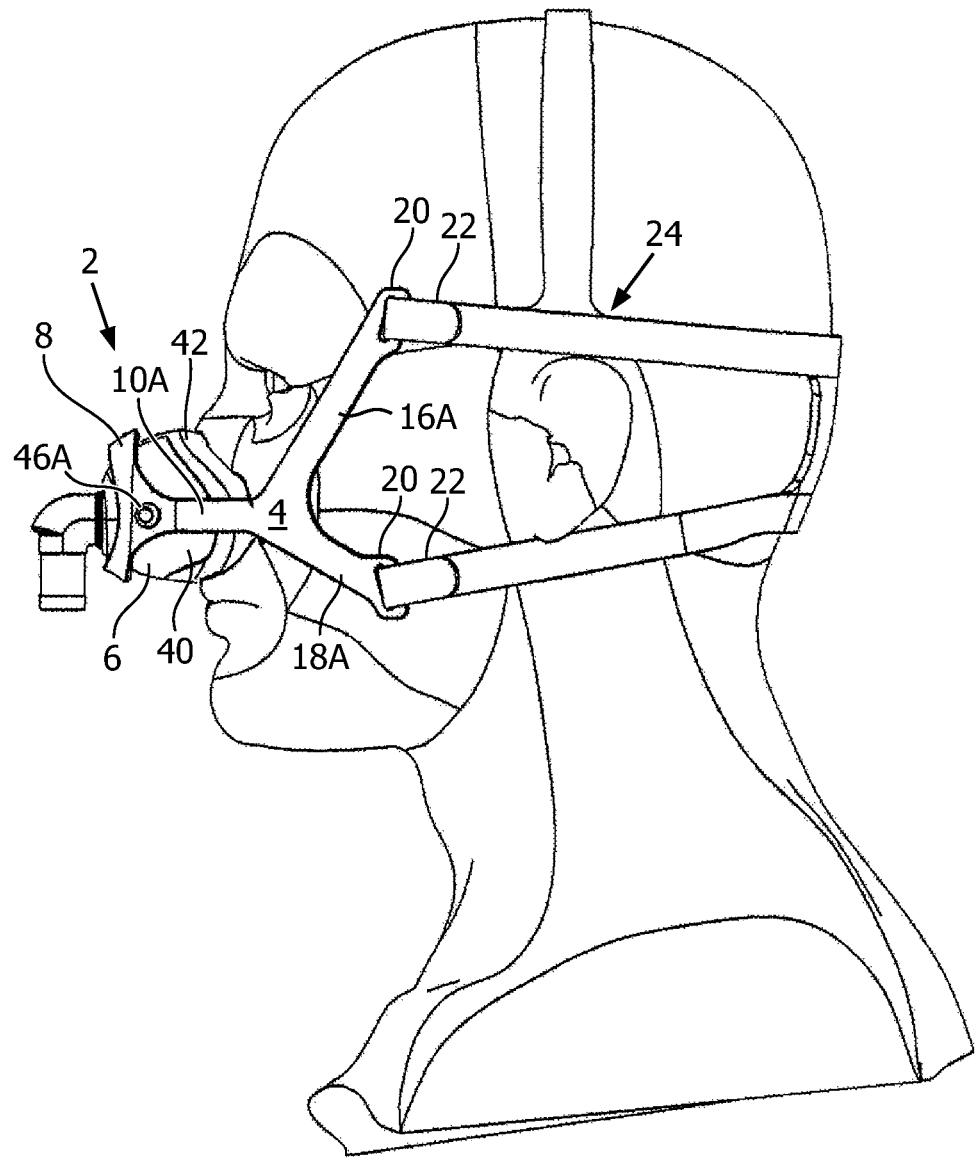
FIG. 9 is a side view and FIG. 10 is an perspective view showing the patient interface device of FIG. 1 attached to a patient.
Figure 10:
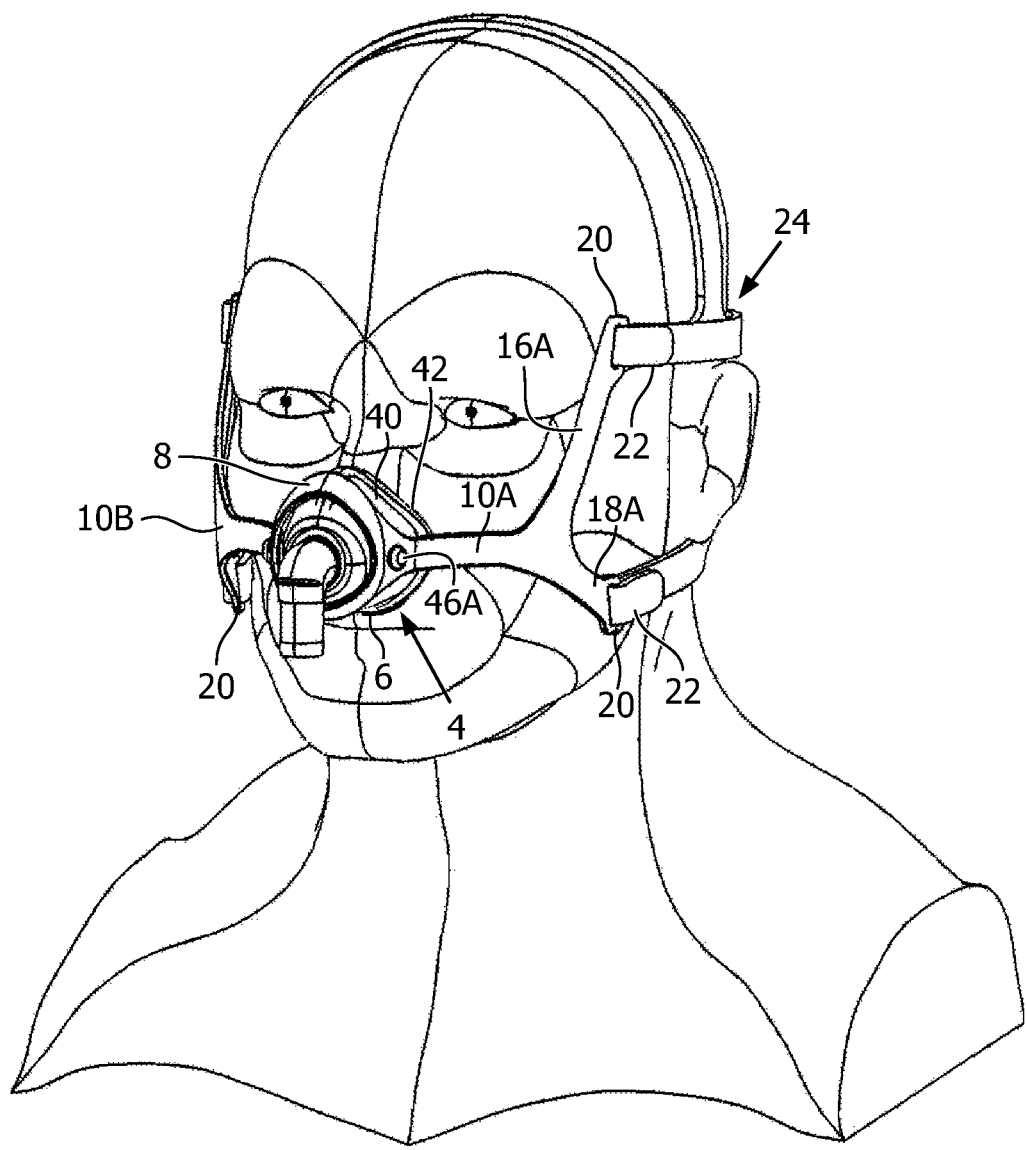

FIG. 1 is a front perspective view of a patient interface device 2 according to an exemplary embodiment of the present invention. FIG. 9 is a side view and FIG. 10 is a front perspective view showing patient interface device 2 attached to a patient. Patient interface device 2 includes a frame member 4 and a cushion 6 coupled to the frame member, each of which is described in greater detail herein.

Figure 2:
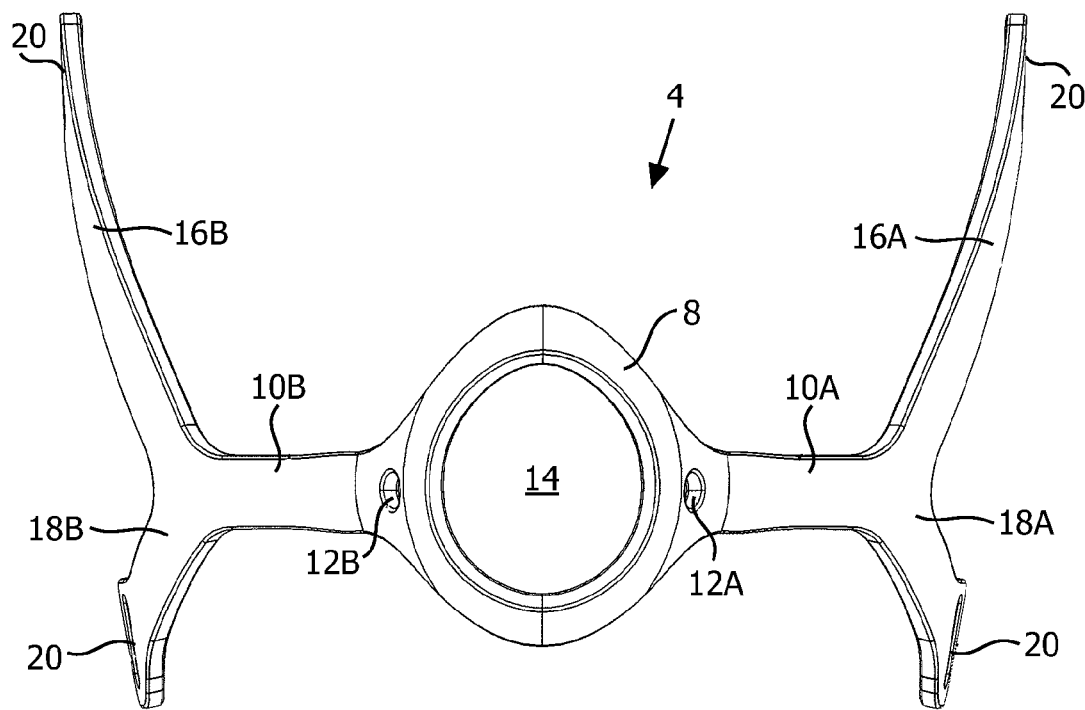
FIGS. 2, 3, 4, and 5 are front, rear, top and side elevational views, respectively, of a frame member of the patient interface device of FIG. 1.
Figure 3:
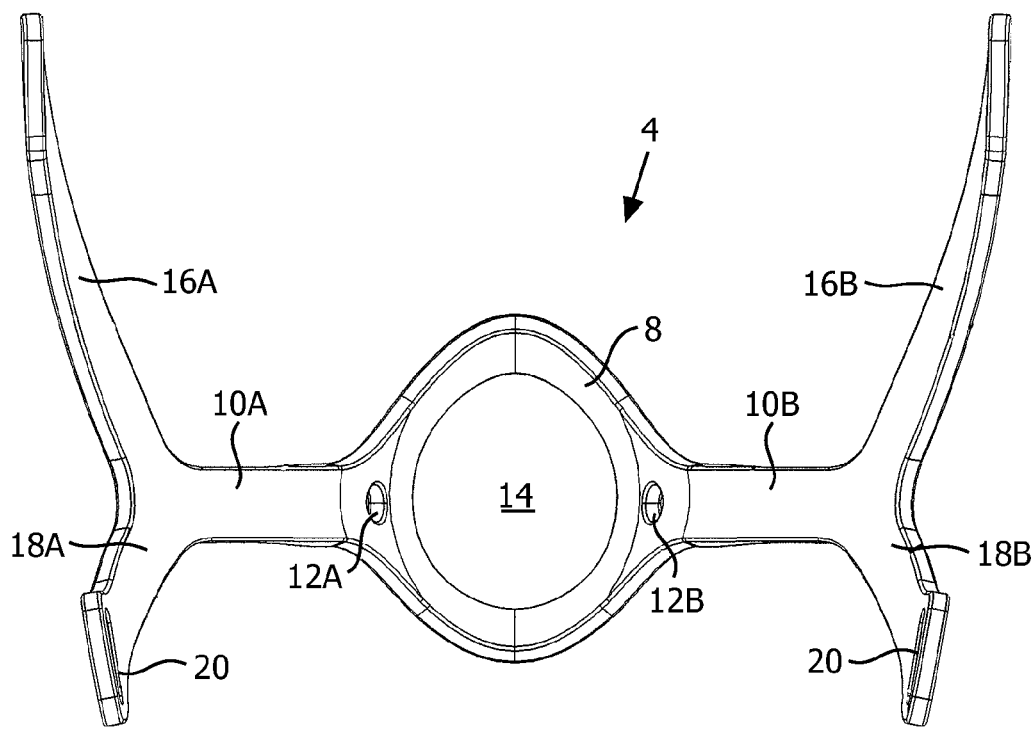

FIGS. 2, 3, 4, and 5 are front, rear, top, and side elevational views, respectively, of frame member 4 of patient interface device 2. Frame member 4 includes a generally annular central member 8 having first and second main arms 10A, 10B extending outwardly from opposites sides thereof. Main arm 10A includes orifice 12A extending therethrough, and main arm 10B includes orifice 12B extending therethrough. In the exemplary embodiment, orifices 12A, 12B are positioned at a location on main arms 10A, 10B adjacent central member 8. The purpose of orifices 12A, 12B is described in detail elsewhere herein. In addition, as seen in FIGS. 2 and 3, central member 8 defines a central orifice 14.

Frame member 4 further includes a first branching member 16A extending upwardly at an angle from main arm 10A and a first branching member 16B extending upwardly at an angle from main arm 10B. In one particular, non-limiting embodiment, first branching members 16A, 16B extend upwardly from the respective main arm 10A, 10B at an angle of about 60 degrees, although other angles are also possible. Furthermore, frame member 4 also includes a second branching member 18A extending downwardly at an angle from main arm 10A and a second branching member 18B extending downwardly at an angle from main arm 10B. In one particular, non-limiting embodiment, second branching members 18A, 18B extend downwardly from the respective main arm 10A, 10B at an angle of about 30 degrees], although other angles are also possible. Also in one particular, non-limiting embodiment, main arms 10A and 10B extend for about 55-60 mm from the center of orifices 12A, 12B to the inner angles formed between the branching members 16A and 18A and 16B and 18B, respectively.

Moreover, as seen in FIGS. 1-5, the distal end of each of first branching member 16A, 16B and second branching member 18A, 18B includes a respective loop member 20 for receiving a respective strap 22 of headgear assembly 24 (FIGS. 9 and 10). In the exemplary embodiment, frame member 4 is made of a thermoplastic or thermoset material.

Figure 6:
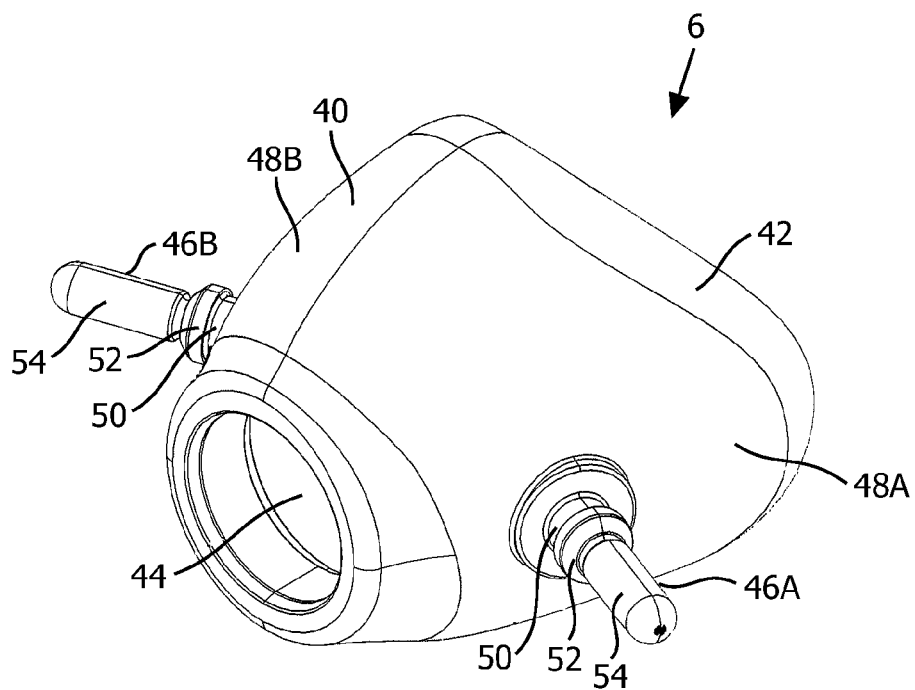
FIGS. 6, 7, and 8 are front isometric, front elevational and rear elevational views, respectively, of the cushion of the patient interface device of FIG. 1.
Figure 7:
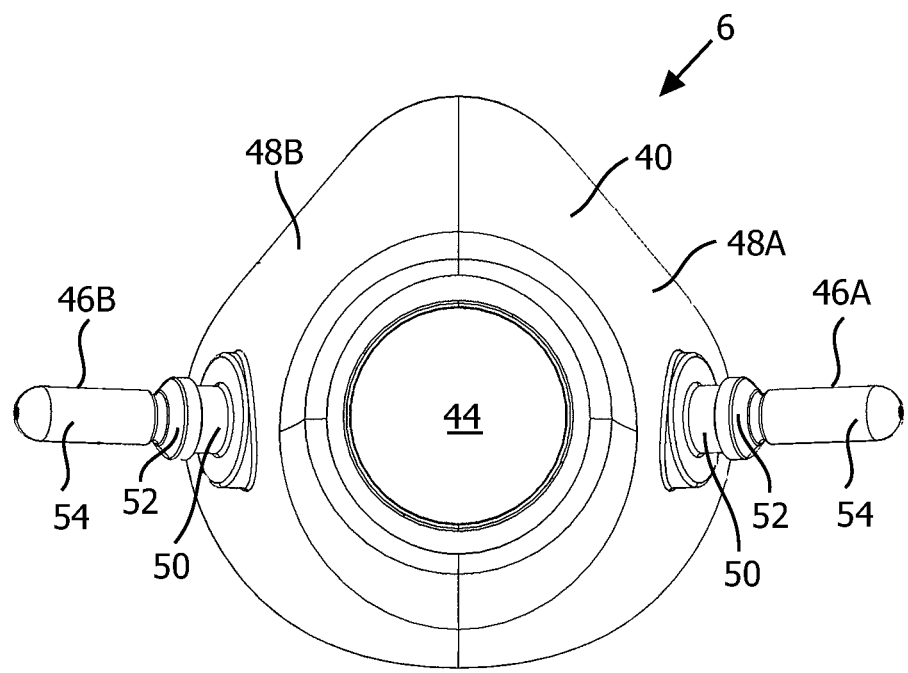
Figure 8:
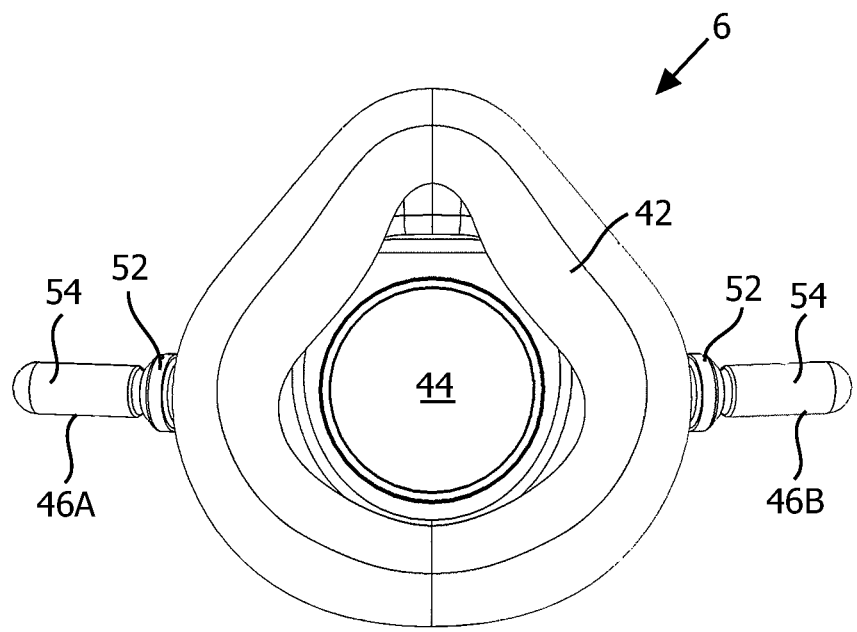

FIGS. 6, 7, and 8 are front isometric, front elevational and rear elevational views, respectively, of cushion 6 of patient interface device 2. In the exemplary embodiment, cushion 6 is defined from a unitary piece of soft, flexible, cushiony, elastomeric material, such as, without limitation, silicone, an appropriately soft thermoplastic elastomer, a closed cell foam, or any combination of such materials. Cushion 6 includes a main body portion 40 having a sealing portion 42 coupled to a first end thereof. Sealing portion 42 is structured to form a seal against a face of the patient. In the illustrated embodiment, cushion 6 is in the form of a nasal mask. However, other types of patient sealing assemblies, such as a nasal/oral mask, nasal cannula, or a nasal cushion, which facilitate the delivery of the flow of breathing gas to the airway of a patient, may be substituted for cushion 6 while remaining within the scope of the present invention.

In addition, main body portion 40 defines an orifice 44 at the second end thereof opposite the first end. Orifice 44 is structured to enable cushion 6 to be fluidly coupled to a fluid connector such as an elbow conduit, which in turn is fluidly coupled a pressure generating device such as a ventilator or a CPAP machine through a gas delivery hose.

Cushion 6 further includes generally cylindrically shaped posts 46A and 46B extending from first and second sides 48A and 48B, respectively, of main body 40. Each post 46A, 46B is positioned about midway between the first and second end of cushion 6. In addition, each post 46A, 46B includes an inner cylindrical portion 50, an enlarged portion 52, and an outer cylindrical portion 54.

When patient interface device 2 is assembled, the second end of main body 40 is inserted through central orifice 14 defined by central member 8. In addition, post 46A is inserted through orifice 12A and post 46B is inserted through orifice 12B. More specifically, as seen in FIG. 1, in each case, outer cylindrical portion 54 and enlarged portion 52 are inserted through the respective orifice 12A, 12B such that each enlarged portion 52 rests against the outer surface of main arm 10A, 10B and prevents outer cylindrical portion 54 from sliding back through orifice 12A, 12B. In addition, each inner cylindrical portion 50 is able to turn within the respective orifice 12A, 12B.

The branching nature of the sides of frame member 4, giving it a "T" or "Y" shape, allows for flexing of frame member 4 in certain directions while at the same time limiting flexing in other directions. In particular, main arms 10A, 10B are able to flex in the directions shown by the arrows in FIG. 4 (i.e., parallel to the top and bottom surface of main arms 10A, 10B), but are not able to freely flex in a direction transverse to the longitudinal axis thereof (i.e., perpendicular to the top and bottom surface of main arms 10A, 10B).

Figure 4:
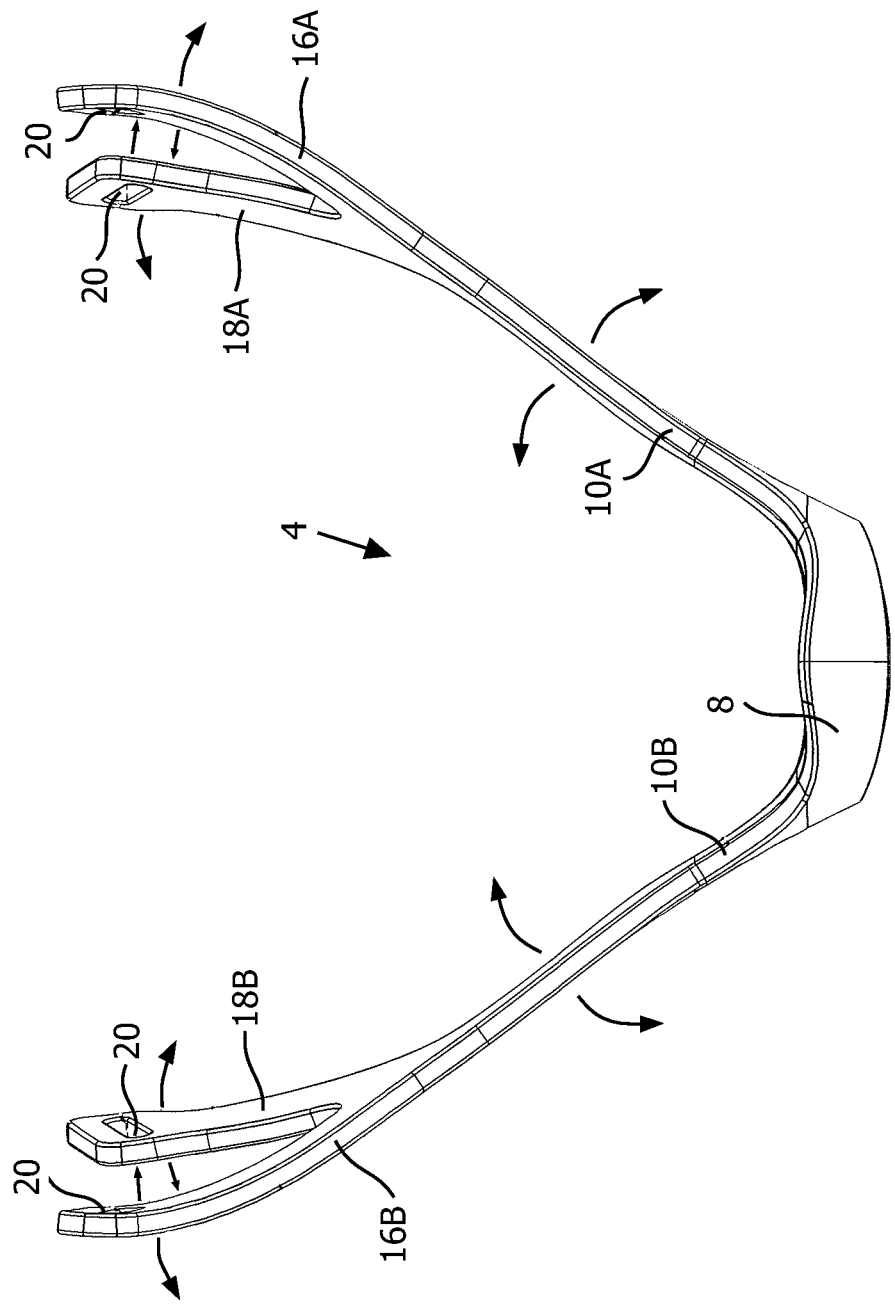
Figure 5:
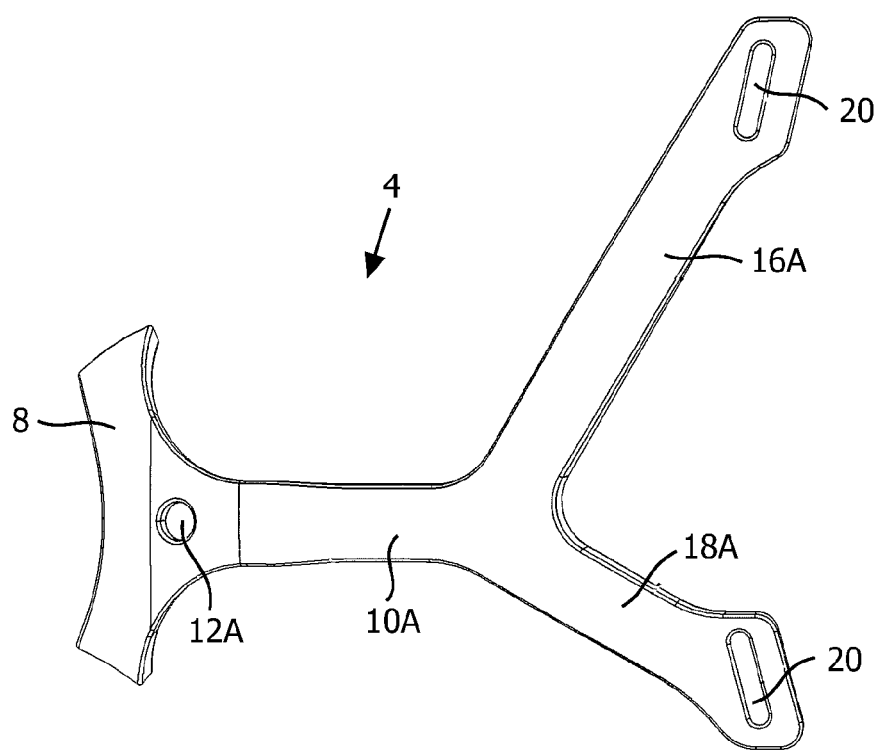

In addition, each of the first branching members 16A, 16B and second branching member 18A, 18B are able to flex independently of one another in the directions shown by the arrows in FIG. 4 (i.e., parallel to the top and bottom surface of the branching members), but are not able to freely flex in a direction transverse to the longitudinal axis thereof (i.e., perpendicular to the top and bottom surface of the branching members). This controlled flexing addresses several issues present in the prior art relating to seal, stability and comfort discussed elsewhere herein, as it passively accommodates for many facial and head geometries to allow for optimal fit and comfort. The branched structure of frame member 4 also increases the stability of patient interface device 2 through patient movement and hose torque, which provides an optimal seal for the patient.

The selection of the material for frame member 4 in conjunction with the geometry of frame member 4 as described herein allows for flexing to accommodate the vast variation in patient facial structures and head dimensions. In the exemplary embodiment, the material will be soft enough to provide for flexing in the desired directions as described herein, but rigid enough to limit the flexing in non-desired directions as described herein. Also, the geometry will, in the exemplary embodiment, allow for accommodation of not only the temple, cheek and jaw regions, but will also cover varying head sizes and nose locations. The geometry of portions of frame member 4 may, for example, vary in thickness, existence of ribs or other structures, and/or general dimensioning to accommodate differences in flexing due to the material properties, but will maintain the branching shape described herein.

Other alternative methods of controlling the direction of flexing of frame ember 4 in the various directions can be accomplished with the use of structures such as hinges incorporated therein. The hinge can be accomplished in a number of different ways, such as with mechanical interlocking (removable or permanent) or overmolding with materials such as silicone or other elastomers.

Furthermore, the branching nature of the sides of frame member 4, giving it the "T" or "Y" shape discussed above, moves the mounting or anchor point (i.e., loops 20) for patient interface device 2 on the head of the patient through headgear assembly 24 further back along the side of the head. Typical mounting locations of nasal masks have been on one or many of the following: cheeks, forehead, and chin. By moving the mounting point away from the front of the face, it improves the issues with claustrophobia and line of sight infringement. It also limits the pressure and potential discomfort from over-tightening to the less sensitive areas of the face.

In addition, the interaction between posts 46A, 46B and orifices 12A, 12B provide the connection point for cushion 6 to frame 4. That connection point provides for a passive auto-adjustment mechanism for cushion 6, as posts 46A and 46B, and thus cushion 6, are able to rotate relative to frame member 4. In the exemplary embodiment, each post 46A, 46B has enough interference with frame member 4 to limit excessive rotation but not enough resistance to prevent auto-adjustment. Also in the exemplary embodiment, the cylindrical shape of each post 46A, 46B, as opposed to an oval or other geometry, allows for an infinite amount of positions instead of discrete positioning. This auto-adjusting feature optimizes the angle of engagement of cushion 6 to the face of the patient and increases the chance for an optimal seal across many patient faces of differing sizes and shapes. It also decreases the chance of undue pressure along the sealing portion 42 of cushion 6 on the face (particularly the upper lip) of the patient. Lastly, this auto-adjusting feature provides the ability of cushion 6 to adjust during patient movement, thus increasing stability throughout the night.

The present invention contemplates that posts 46A, 46B are formed from the same material as cushion 6. In this embodiment, the cushion and posts may be molded as a unitary structure to simplify manufacture. The present invention also contemplates that the posts may be formed from a different material (or combination of materials that differ) from cushion 6. The present invention contemplates that the post are flexible and/or the connection of the posts to the cushion is a flexing joint to provide even further passive adjustment of the cushion relative to frame member 4.

Thus, the combination of the flexing frame member 4 and the auto-adjusting cushion 6 allows for placement of frame member 4 on the face to vary in order to meet the individual patient's needs. This allows an opportunity for the patient to alleviate any possible pressure points and/or optimize seal and stability. In addition, the mounting point of cushion 6 to frame member 4 has been moved closer to the patient's face, which increases the stability of patient interface device 2 by moving the fulcrum closer to the patient's face (moment arm decreases). It also lessens the overall profile of patient interface device 2, creating a lower profile that improves overall size and appearance.

Moreover, while cushion 6 has, for illustrative purposes, been described herein in connection with the particular flexing frame member 4, it is to be understood that the present invention is not limited to use with such a frame member and that cushion 6 may be used with and coupled to other, alternative frame members having alternative configurations and shapes without departing from the scope of the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
   a frame member defining a first orifice and a second orifice, the frame member including a generally annular central member defining a central orifice, a first main arm that extends from a first side of the central member and a second main arm that extends from a second side of the central member;
   a cushion having a main body, a sealing portion provided at a first end of the cushion, and a first post extending from a first side of the main body and a second post extending from a second side of the main body, wherein the cushion is a unitary structure, wherein a second end of the cushion opposite the sealing portion defines a fluid coupling orifice, wherein the second end of the cushion including the fluid coupling orifice is inserted through the central orifice of the central member of the frame member, and wherein the first post is rotateably received within the first orifice and the second post is rotateably received within the second orifice in a manner that permits the cushion to rotate relative to the frame member; and a fluid connector having a first end structured to be connected to a source of breathing gas and a second end opposite the first end, wherein the second end of the fluid connector is selectively received within the fluid coupling orifice in a manner wherein the second end of the fluid connector directly contacts the second end of the cushion.

2. The patient interface device according to claim 1, wherein the first post and the second post are each provided on the main body at a respective position about midway between the first end and the second end of the cushion.

3. The patient interface device according to claim 1, wherein the first orifice and the second orifice are circular and the first post and the second post are cylindrical.

4. The patient interface device according to claim 3, wherein the first post and the second post each include an inner cylindrical portion, an outer cylindrical portion, and an enlarged portion provided between the inner cylindrical portion and the outer cylindrical portion.

5. The patient interface device according to claim 1, wherein the first main arm includes a first branching member extending upwardly from a first end of the first main arm and a second branching member extending downwardly from the first end of the first main arm, and the second main arm includes a third branching member extending upwardly from a first end of the second arm and a fourth branching member extending downwardly from the first end of the second main arm.

6. The patient interface device according to claim 5, wherein the first orifice is provided in a second end of the first main arm and the second orifice is provided in a second end of the second main arm.

7. The patient interface device according to claim 5, wherein the first main arm has a first outer surface, a first inner surface, a first top edge and a first bottom edge, wherein the first main arm is free to flex in a direction that is generally parallel to the first top edge and the first bottom edge, and is not free to flex in a direction that is generally perpendicular to the first top edge and the first bottom edge, wherein the first branching member has a second outer surface, a second inner surface, a second top edge and a second bottom edge, wherein the first branching member is free to flex in a direction that is generally parallel to the second top edge and the second bottom edge, and is not free to flex in a direction that is generally perpendicular to the second top edge and the second bottom edge, and wherein the second branching member has a third outer surface, a third inner surface, a third top edge and a third bottom edge, wherein the second branching member is free to flex in a direction that is generally parallel to the third top edge and the third bottom edge, and is not free to flex in a direction that is generally perpendicular to the third top edge and the third bottom edge.

8. The patient interface device according to claim 5, wherein the first main arm and the second main arm are structured to extend horizontally from the central member when the patient interface device is donned by a patient.

9. The patient interface device according to claim 8, wherein the first and third branching members are structured to be positioned behind the eyes of the patient and the second and fourth branching members are structured to be positioned behind the mouth of the patient when the patient interface device is donned by the patient.

10. The patient interface device according to claim 9, further comprising a plurality of connector members, wherein each of the first, second, third and fourth branching members includes a respective one of the connector members for connecting to a respective strap of a headgear assembly.

11. A cushion for a patient interface device, comprising:
a main body;
a sealing portion provided at a first end the main body, wherein a second end of the main body opposite the sealing portion defines a fluid coupling orifice structured to be coupled to a fluid connector;
a first post extending from a first side of the main body and structured to be rotateably received within a first orifice of a frame member of the patient interface device; and
a second post extending from a second side of the main body and structured to be rotateably received within a second orifice of a frame member of the patient interface device, wherein the first post and the second post each include an inner portion, the inner portion being a first cylinder, wherein a diameter of the first cylinder is a first value, an outer portion, the outer portion being a second cylinder, wherein a diameter of the second cylinder is a second value, and an enlarged portion provided between the inner portion and the outer portion, wherein a diameter of the enlarged portion is a third value, and wherein the third value is greater than the first value and the second value.

* * * * *